United States Patent [19]

Quenin

[11] Patent Number: 5,053,198
[45] Date of Patent: Oct. 1, 1991

[54] USED TEST ELEMENT COLLECTION APPARATUS AND METHOD

[75] Inventor: John A. Quenin, Rochester, N.Y.

[73] Assignee: Eastman Kodak Company, Rochester, N.Y.

[21] Appl. No.: 358,527

[22] Filed: May 26, 1989

Related U.S. Application Data

[63] Continuation-in-part of Ser. No. 310,133, Feb. 14, 1989, abandoned.

[51] Int. Cl.⁵ .................. G01N 35/00; B65D 85/48
[52] U.S. Cl. .................................. 422/64; 422/63;
422/102; 422/104; 436/46; 206/456; 206/425;
206/817; 53/244; 53/284.2; 53/284.4
[58] Field of Search .................. 422/63, 64, 102, 104;
436/46; 206/456, 425, 817; 53/244, 284.2,
284.4; 414/794.7, 799

[56] References Cited

U.S. PATENT DOCUMENTS

| | | | |
|---|---|---|---|
| 3,992,158 | 11/1976 | Przybylowicz et al. | 422/57 |
| 4,053,381 | 10/1977 | Hamblen et al. | 204/195 M |
| 4,190,420 | 2/1980 | Covington et al. | 422/63 |
| 4,295,565 | 10/1981 | Takeuchi | 206/817 |
| 4,424,191 | 1/1984 | Jakubowicz | 422/63 |
| 4,473,154 | 9/1984 | Ackeret | 206/817 |
| 4,512,952 | 4/1985 | Blanding | 436/46 |
| 4,766,714 | 8/1988 | Sugaya | 53/242 |
| 4,817,820 | 4/1989 | Heiland | 206/817 |

Primary Examiner—Robert J. Warden
Assistant Examiner—Theresa A. Trembley
Attorney, Agent, or Firm—Dana M. Schmidt

[57] ABSTRACT

There are described apparatus for collecting used test elements containing possibly hazardous liquids, and a method of collecting them. The apparatus features a container, and preferably a stacking station used with the container. The container can comprise a variety of configurations, and includes side walls, first and second end walls, access means in one of the side walls near the first end wall defining an aperture to allow test elements to feed into the container, and biasing means for biasing a test element against the first end wall or against a test element adjacent to the first end wall. A highly preferred form of the container is one in which one of the noted side walls is constructed to be a leaf spring.

As to the method of collecting, it comprises the steps of a) inserting the first used test element into the container adjacent one end and under the biasing means so that a portion of the first element projects from the container; b) inserting the next used test element into the container under the first test element by inserting it under the projecting portion and pushing the first test element against the biasing means; and c) inserting successive used test elements into the container so that they each enter under the last one in, until the container is full.

18 Claims, 9 Drawing Sheets

USED TEST ELEMENT COLLECTION APPARATUS AND METHOD

This is a continuation-in-part of application Ser. No. 310,133, filed Feb. 14, 1989, now abandoned.

FIELD OF THE INVENTION

The invention is directed to apparatus useful for collecting in a container members that need to be collected in an orderly fashion, and particularly used test elements of a blood analyzer. It is particularly addressed to such apparatus designed to be used in zero-gravity environments.

BACKGROUND OF THE INVENTION

Clinical analyzers have long tested so-called "dried" test elements, wherein the reagents for the test are in a porous matrix in dried form. Examples are shown in U.S. Pat. Nos. 3,992,158 and 4,053,381. Conventionally, it has been the practice to incubate test elements containing patient sample, read them at a read station that detects changes that occur in proportion to the amount of analyte present that is being tested for, and discard them. The discard has conventionally involved a chute or container of some kind in which the test elements fall in loose disarray. The operator occasionally empties the chute or discard container, and loose test elements in such containers are susceptible to falling out or spilling onto the operator or apparatus. Until recently, such occasional risk of a used test element falling out, has not been a serious drawback. However, there are several reasons now why such a discard procedure is inadequate.

First, in Earth-based analyzers, there is the potential for hazardous wastes to be present in the test element. If blood, a common biological liquid for test, is present, the test element can be contaminated with such things as hepatitis B virus, a highly contagious virus, or other equally serious viruses. The operator does not want such used elements contacting his skin.

Second, in space-station analyzers, zero-g environments mean that test elements discarded in a loose fashion have the risk of floating anywhere. The result can be that loose, used test elements will contaminate or even jam other equipment.

Therefore, there has been a substantial need prior to this invention for collection apparatus for used test elements that will keep such test elements in a container that provides a confined environment, one in which the used test elements remain in an ordered array.

SUMMARY OF THE INVENTION

I have constructed such collection apparatus and provided an analyzer improved in that it uses such apparatus.

More specifically, in accord with one aspect of the invention there is provided an automatic collection apparatus for test elements used in an analyzer to measure analytes in a biological liquid, the apparatus comprising a container having side walls, first and second end walls, access means in one of the side walls near the first end wall defining an aperture to allow test elements to feed into the container, and biasing means for biasing a test element against the first end wall or against a test element adjacent to the first end wall; and a stacking station for inserting test elements into the container, the station including means for releasably holding the container in position to receive used test elements, and guide means for guiding used test elements into the container in an ordered array. Preferably such guide means comprise a stationary track, means for mounting the stacking station for limited vertical movement with respect to the track, between first and second limits; and means for biasing the stacking station against one of the limits, the stacking station including a camming surface shaped and positioned relative to the track to cause the stacking station a) to move against the biasing means when a test element first contacts the camming surface from the track, b) to receive the contacting test element, and c) to allow the stacking station to return under the action of the biasing means after loading the contacting test element, with the loaded test element positioned out of the plane of the track, whereby used test elements are loaded in the ordered array.

In accord with another aspect of the invention, there is provided an analyzer for testing analytes in a liquid patient sample in a test element containing reagents, the analyzer including means for incubating a test element to which a patient sample has been added, means for reading a detectable signal generated by a test element in response to the added patient sample, and means for moving a test element through the analyzer, including from the incubating means to the reading means. The analyzer is improved in that it further includes automatic collection apparatus disposed downstream from the reading means to receive used test elements from the reading means, the apparatus comprising the container and stacking station noted in the previous paragraph.

In accord with yet another aspect of the invention, there is provided a method of collecting used test elements in an ordered array as they exit from a read station in an analyzer to a collection container having a hold-down spring. The method comprises the steps of a) inserting the first used test element into the container adjacent one end and under the spring so that a portion of the first element projects from the container; b) inserting the next used test element into the container under the first test element by inserting it under the projecting portion and pushing the first test element against the spring; and c) inserting successive used test elements into the container so that they each enter under the last one in, until the container is full.

In accord with still another aspect of the invention, there is provided a container for holding stackable members, comprising two opposing end walls, one of which is constructed to contact a member stacked in the container, a side wall joining the end walls, and opposite to the side wall, as the sole side wall on that side of the container, a leaf spring extending from one of the end walls towards, but not joined with, the opposite end wall.

Thus, it is an advantageous feature of the invention that used test elements are collected in a container that holds them in an ordered array, preventing spillage of such elements as would either contaminate the surrounding environment or risk infecting the operator with viruses in the patient sample.

Other advantageous features will become apparent upon reference to the following description of the preferred embodiments, when read in light of the attached drawings.

DESCRIPTION OF THE PREFERRED EMBODIMENTS

The invention is described hereinafter with respect to the preferred embodiment that is a complete analyzer that uses dried test elements, and particularly one that can be used in zero-G environments. In addition, it is useful in any apparatus where used members need to be collected, regardless of whether the apparatus is a complete analyzer. It is also useful in earth-bound apparatus to avoid the danger of contaminating the equipment or operator with patient sample. It is further useful in assemblying unused elements in a container that is to be loaded into an analyzer.

Descriptors such as "up", "down" and the like refer to orientations of use as they are shown in the attached drawings. As will be readily apparent, such orientations tend to be arbitrary if the apparatus is being described for use in zero gravity. Furthermore, the analyzer described herein will operate in any orientation, even in a 1-G environment.

Figure 1:
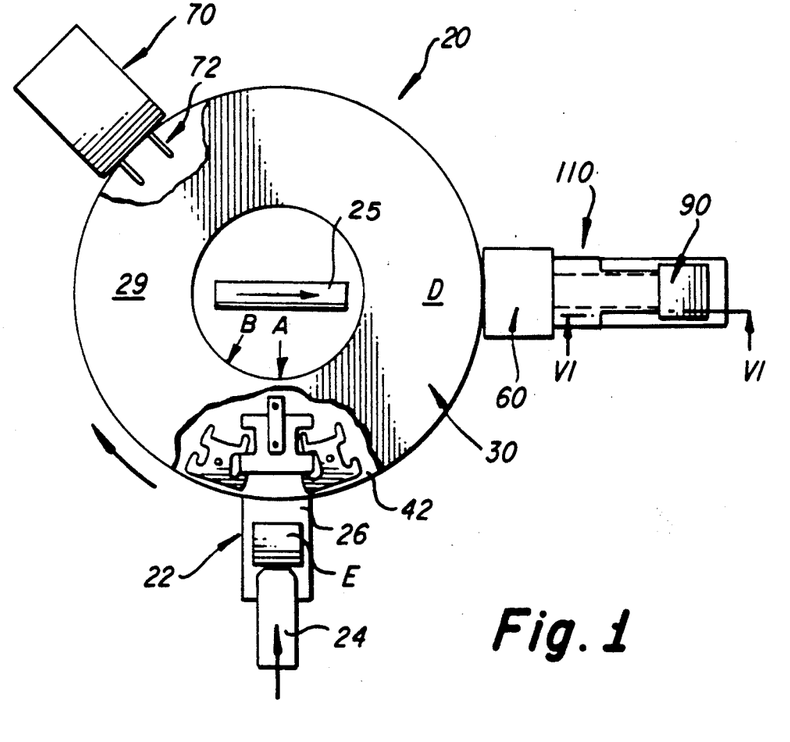
FIG. 1 is a partially broken away, partially schematic plan view of an analyzer constructed in accordance with the invention.

Referring to FIG. 1, an analyzer 20 constructed in accord with the invention comprises a sample-dispensing station 22, an incubator 30, means 24 for transferring test elements E containing patient sample, from station 22 into the incubator, a potentiometric read station 70 disposed adjacent to one side of incubator 30, a colorimetric read station 60, also disposed adjacent to the incubator and displaced circumferentially from read station 70, a container 90 to receive used test elements, a guide 110 to direct such used test elements from read station 60 to container 90, and transfer means 25 for transferring a test element from incubator 30 to read station 60 and then to guide 110 and container 70. Most preferably, transfer means 24 and 25 are pusher blades activated and guided in a conventional manner by motors, etc., not shown, moved over support surfaces such as surface 26.

Considering first the conventional parts of the analyzer, any suitable liquid dispensing means (not shown) is useful at station 22. Such station 22 also includes suitable structure (not shown) that restricts test element E to movement generally in contact with surface 36, particularly when used in a zero-G environment.

Figures 2, 3:
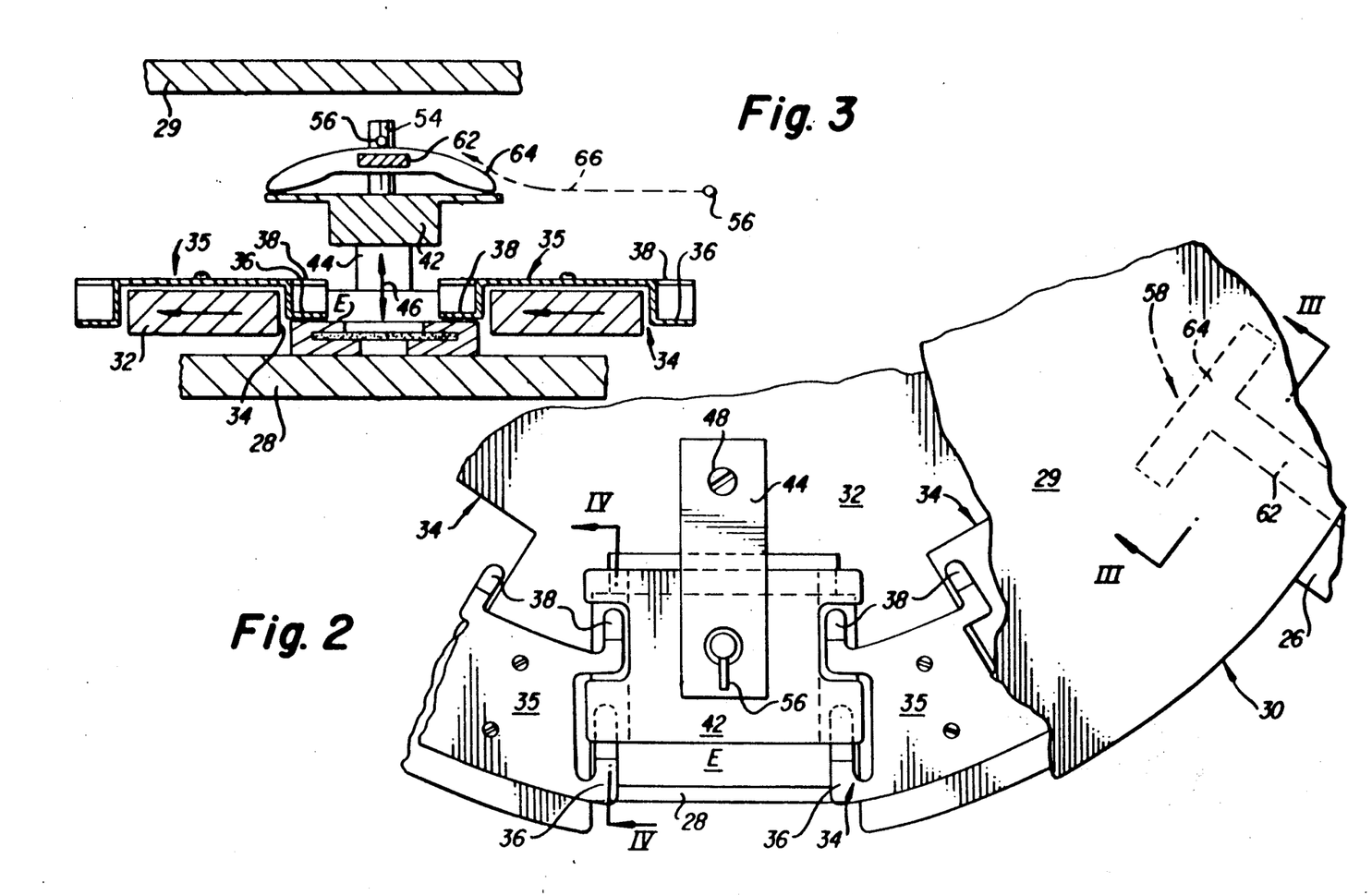
FIG. 2 is a fragmentary, enlarged plan view similar to that of FIG. 1, illustrating greater detail.
FIG. 3 is a fragmentary section view taken generally along the line III—III of FIG. 2.

Incubator 30 features a stationary lower support plate 28, FIGS. 2-3, and a stationary upper cover plate 29. Either or both of these plates are heated in a conventional manner, with sensors, not shown, to provide feedback to control the incubator temperature as desired. Mounted between plates 28 and 29, FIGS. 2 and 3, is a rotor 32 providing individual test-element holding stations formed as pockets in the rotor. More specifically, indentations 34 are formed in rotor 32, and hold-down leaf springs 35 are attached along the periphery of each indentation. The indentations are shaped and sized to hold a test element E therein, and springs 35 are shaped to press a test element against lower support plate 28, FIGS. 3 and 4. Preferably, springs 34 are dual springs that extend over the top of rotor 32, with a pair of fingers 36, 38 adjacent each indentation 34. Additionally, an evaporation cap 42 is provided, FIGS. 2 and 3, that is attached via a leaf spring 44 to rotor 32 to permit limited vertical movement, FIG. 3, arrow 46, of cap 42. Spring 44 is attached at 48 to rotor 32 and presses down on cap 42. A rod 54 rises out of cap 42, with a cam follower pin 56 that functions as described below.

As described in commonly-owned application Ser. No. 293,718 cofiled by Johannes Porte, entitled "Incubator and Analyzer with Improved Cap Raising Means", to raise cap 42 when rotor 32 moves an indentation 34 on plate 28 to receive a test element, FIGS. 2 and 3, a cam 58 is provided, shown in phantom in FIG. 2. Cam 58 comprises a bridge element 62 fixed to the analyzer and a ramp 64. The shape of ramp 64 is constructed to cam pin 56 upward, and thus raise cap 42, as shown by arrow 66, FIG. 3.

Regarding potentiometric read station 70, FIG. 1, such station is conventional, and features a pair of electrodes 72 that raises and lowers into contact with appropriate parts of ISE (Ion Selective Electrode) test elements held by rotor 32. That station is not activated until an ISE test element is positioned thereunder, ready for reading, as controlled by a suitable microprocessor, not shown. (Detection of which kind of test element is at which indentation 34 is done by a bar code reader at station 22, not shown.)

A similar camming mechanism is preferably present at station D. That is, all test elements are removed and sent through read station 60. If the element is a potentiometric element already read at station 70, the detector at 60 is simply turned off for that particular test element.

Figures 4, 5:
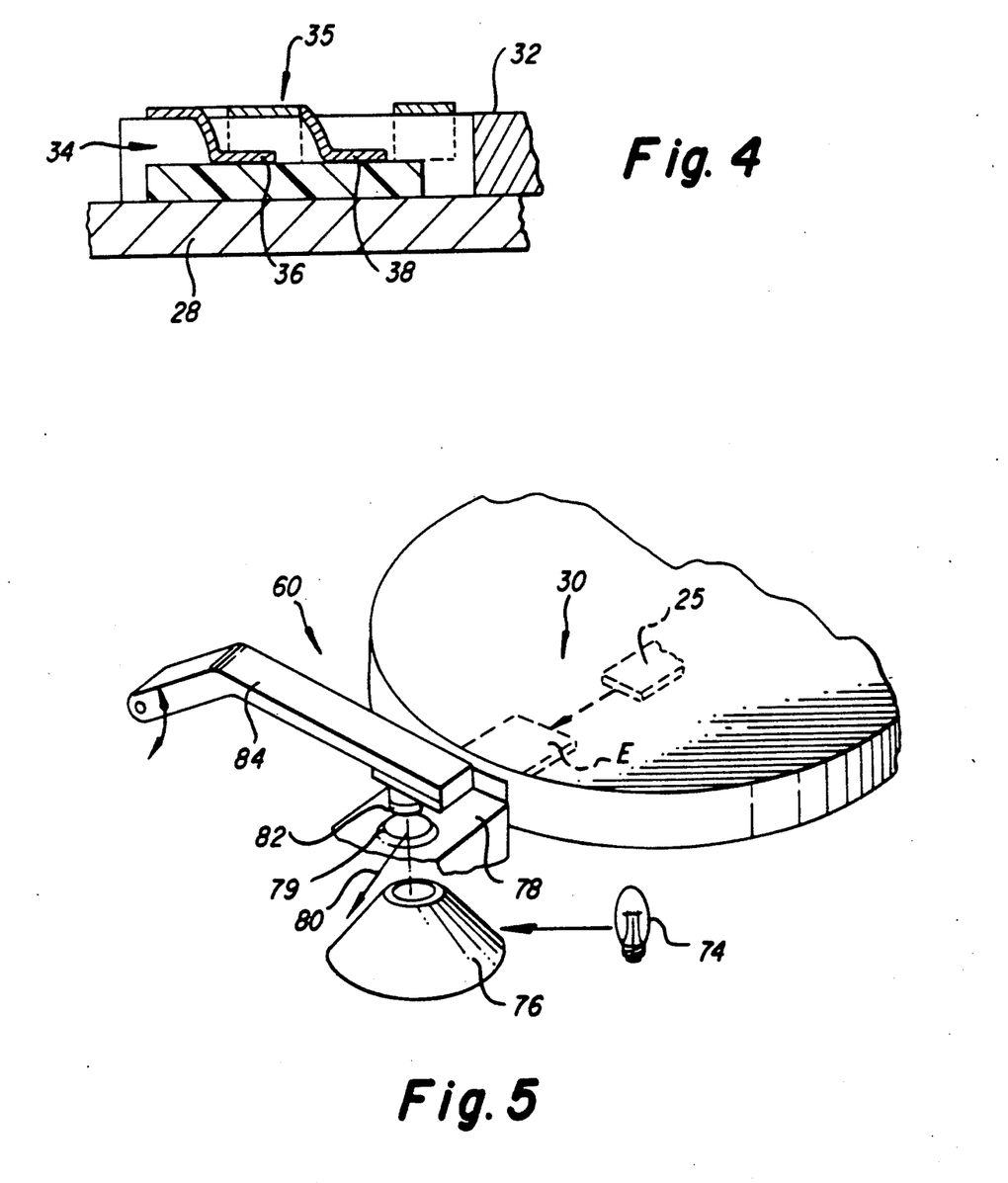
FIG. 4 is a fragmentary section view taken along the line IV—IV of FIG. 2.
FIG. 5 is a fragmentary, partially schematic perspective view of the read station of the analyzer.

With respect to colorimetric read station 60, such station is conventional and features, FIG. 5, an appropriate light source 74 with optics, not shown, directing light to illuminating means 76, which is preferably an integrating surface, for example, the type disclosed in U.S. Pat. No. 4,660,984 (MacDonald). A support surface 78 is provided with a transparent window 79, over which a test element E is moved via appropriate pusher blades, such as blade 25. Light reflected from the element as beam 80 is then read via an appropriate detector, not shown. A cover 82 is positioned to hold element E in place for reading. Cover 82 is mounted on a raisable arm 84.

In accord with one aspect of the invention, a container 90 is provided for used test elements. Such container comprises, FIG. 6, an end wall 92, shown as a "bottom" wall, an end wall 94, FIGS. 6 and 7, opposite to wall 92, and pairs of side walls 96, 96' and 98, 98', wherein the members of each pair are opposing. An access aperture 100 is formed in one of the side walls 96'.

Figure 6:
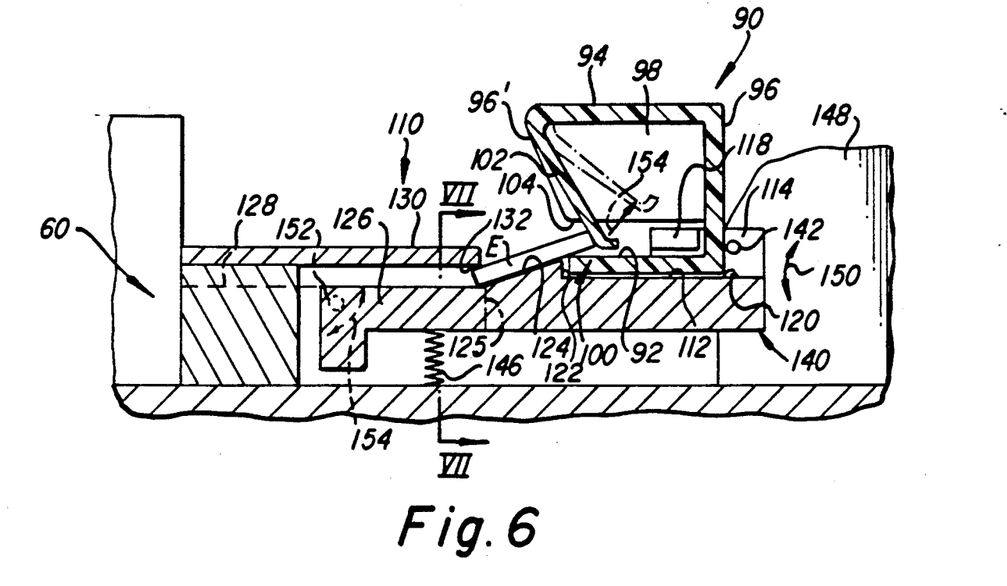
FIG. 6 is a fragmentary section view taken generally along the line VI—VI of FIG. 1.

Importantly, hold-down spring bias means 102 are provided within container 90, and preferably such means comprise all of side wall 96' above aperture 100 formed in it. That is, side wall 96' preferably comprises a leaf spring, which in its uncompressed state projects inwardly towards side wall 96 from its hinged connection at end wall 94.

A notch 104 is provided in each of side walls 98, 98', to releasibly engage the stacking station as described below.

Figure 7:
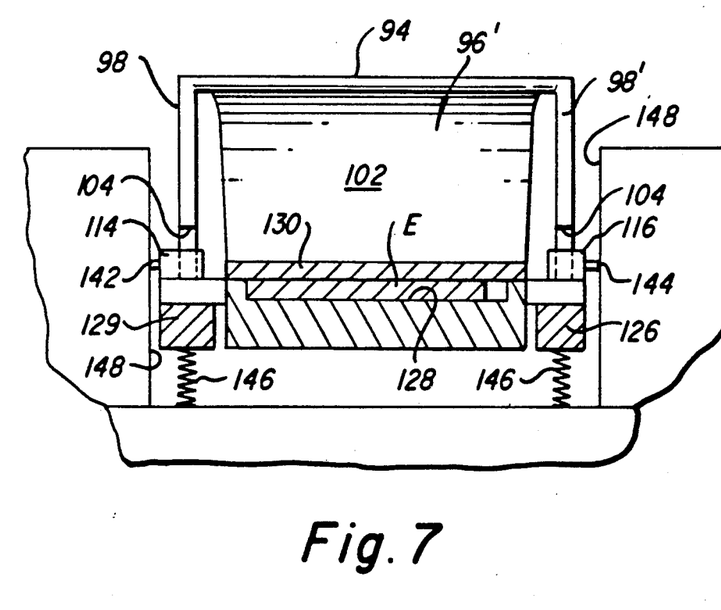
FIG. 7 is a fragmentary section view taken along the line VII—VII of FIG. 6.

In accord with another aspect of the invention, to cause used test elements to properly stack within container 90, a stacking station 110 is provided, FIGS. 1, 6 and 7. Station 110 comprises a frame 140 providing a support surface 112, FIG. 6, for receiving end wall 92 of container 90, and shoulders 114 and 116 for confining side walls 98 and 98', respectively, FIG. 7. Shoulders 114 and 116 include inwardly projecting lips 118 that slip into notches 104 to press against the upper surface, FIG. 6, of end wall 92. A spring-biased ball detent 120 causes container 90 to snap into its held position at one end of surface 112.

At the opposite end of surface 112, an abutment 122 is formed against which end wall 92 is pushed. Station 110 further includes a ramp surface 124. Surface 124 terminates at an edge 125, FIG. 6, which is positioned closely adjacent to the aperture 132 of the stationary guide surface 128, described hereafter. The rest of station 110 comprises a yoke formed by two arms 126, 129 that extend alongside a guide surface 128, FIG. 7.

Guide surface 128 exits from read station 60, FIG. 6. To keep test elements from moving out of contact with guide surface 128, such as when the analyzer is used in the absence of gravity, a restricting cover 130 extends above surface 128, spaced a distance allowing test elements to slide from station 60 to container 90. Cover 130 terminates at an aperture 132, sized to allow a test element E to tilt upward as such a test element proceeds up ramp surface 124. The importance of the incline so provided to the test element will be apparent from the method of use set forth hereinafter.

Figure 8:
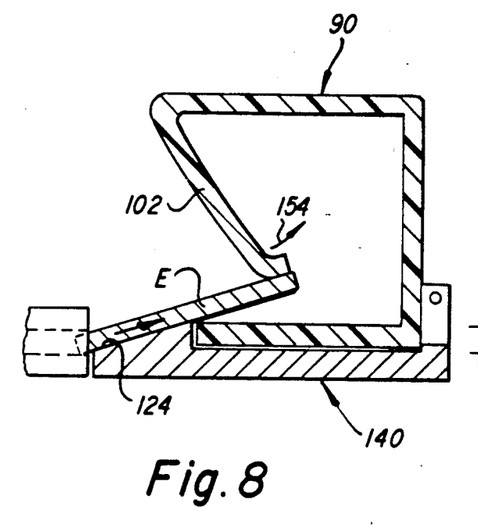
FIGS. 8-11 are section views similar to that of FIG. 6, illustrating the operation of the stacking station.

Both stacking station 110 and its captured container need to have a slight vertical movement. To this end, frame 140 is pivotally mounted at opposite points 142, 144, FIGS. 6 and 7, to the rest of the analyzer, shoulders 148. Compression springs 146 bias surfaces 112 and 124 to the position shown in FIGS. 6 and 8. Springs 146 act to resist the slight downward pivoting movement, arrow 150, FIG. 10, caused as a test element first starts up ramp surface 124 as it protrudes out of aperture 132.

Alternatively, the pivoting of the frame 140 of stacking station 110 can be at points 152, shown in phantom, FIG. 6, so that the pivoting occurs as shown in arrow 154.

Figure 10:
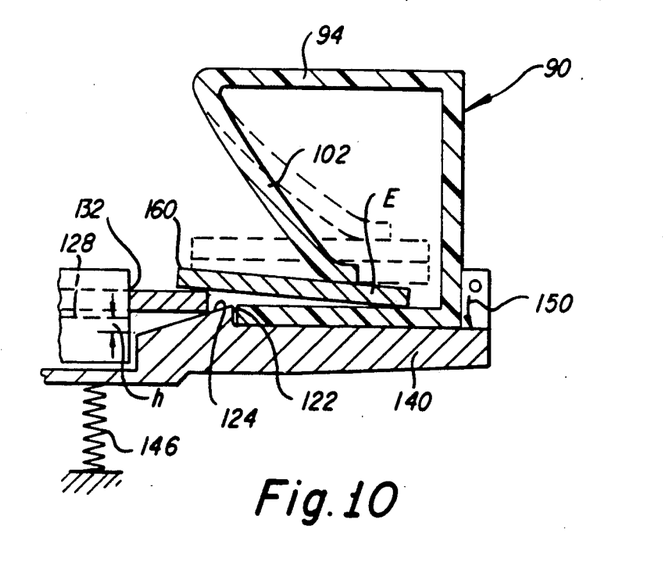

The method of use will be readily apparent from the above description. The used slides are collected as follows: As they exit from read station 60, they slide along surface 128, under cover 130. Ramp 124, FIG. 10, is encountered when a used test element starts to exit aperture 132. This encounter presses the test element against the undersurface of cover 132, and the test element in turn forces surface 124 and frame 140 to pivot down slightly, distance h and arrow 150, against springs 146, as described. (Distance h increases until element E clears abutment 122.) If the element so advancing is the first element, it proceeds up ramp surface 124, through aperture 100, forcing spring 102 upward and back, arrow 154, FIGS. 6 and 8. When element E reaches the position shown in FIG. 8, the downward pressure on frame 140 is released, and it rises to its position shown in FIGS. 6 and 8, where it is held by a stop (not shown) from further upward pivoting.

Figure 9:
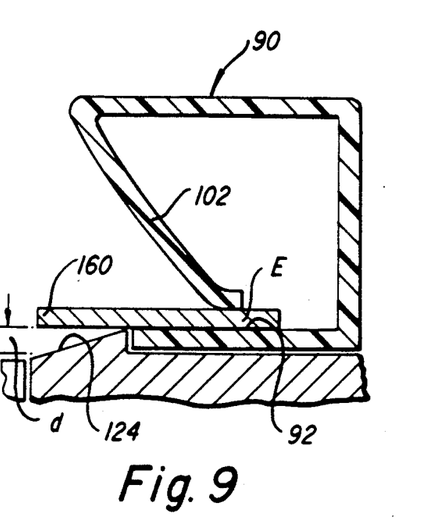
Figure 11:
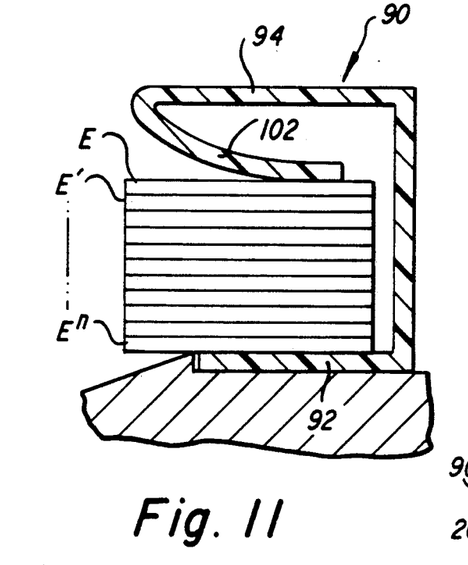

Once the first element E is fully within container 90, FIG. 9, it sits on end wall 92 so that a portion 160 of that element projects from container 90, with a predetermined distance "d" between its lower surface, and the ramp surface 124. Distance "d" is selected to be sufficient to accommodate a second test element E', under portion 160, FIG. 10, as the second element advances up ramp 124. As a result, first element E is pushed against spring 102 so that element E' can be stacked under element E. (The downward pivotal movement of frame 140, FIG. 10, and container 90 held therein, aids in making room for element E' as it pushes element E against hold-down spring 102 of container 90.) In like fashion, successive elements coming from read station 60 are inserted into container 90, so that spring 102 continues to be pressed toward end wall 94, as it is shown in phantom, FIG. 10. When container 90 is full, the first element E is in contact with spring 102, FIG. 11, and the last element $E^n$ is in contact with end wall 92, with intermediate elements in serial array inbetween. At this point, container 90 is simply pulled out against the biased detent 120, with the used elements still in place, and wrapped up and discarded. An empty container is put in its place.

Figure 12:
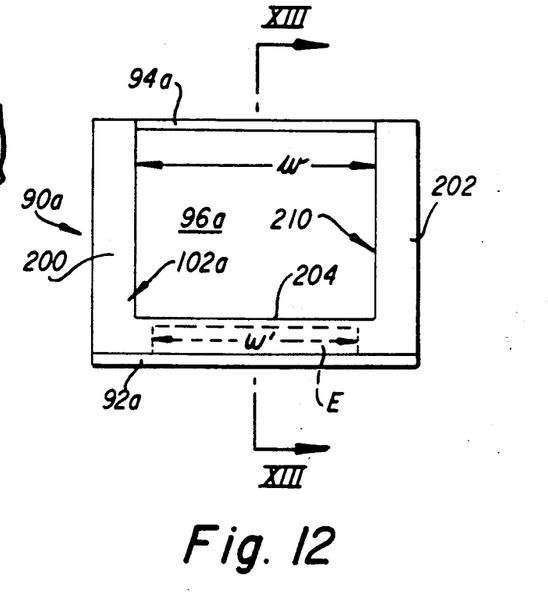
FIG. 12 is a front elevational view similar to that of FIG. 7, but of an alternate embodiment of the container.
Figure 13:
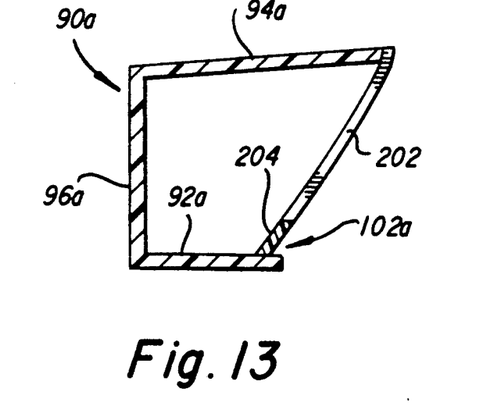
FIG. 13 is a section view similar to that of FIG. 6 but illustrating an alternative embodiment.
Figure 14:
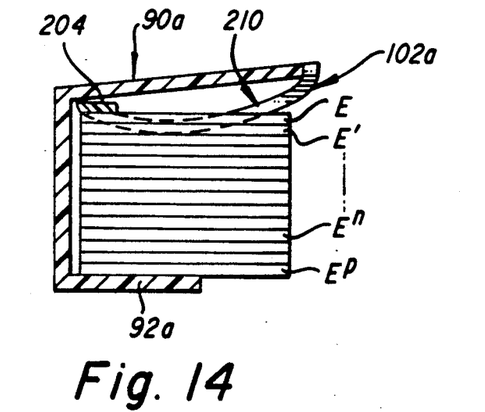
FIG. 14 is a section view similar to that of FIG. 13, illustrating an advantage of this embodiment.

To allow for more elements to be stacked before a container is full, it is not essential that wall and hold-down spring 102 be a solid piece. As shown in the embodiment of FIGS. 12–14, it can have an aperture designed to allow additional elements to be present. Parts similar to those previously described bear the same reference numeral, to which the distinguishing suffix "a" has been appended.

Thus, FIGS. 12 and 13, container 90a comprises end walls 92a and 94a, and leaf spring 102a extends downward from wall 94a as before. However, side walls 98 and 98' are omitted, there only being side wall 96a to join end wall 92a with end wall 94a. Most importantly, leaf spring 102a is U shaped, comprising downwardly extending legs 200, 202 and a cross-member 204 connecting them, providing a large window 210 with a width "w", FIG. 12.

The advantage of window 210 can be seen in FIG. 14. As elements E, E' ... $E^n$ stack into place, one by one in sequential array, instead of becoming full when leaf spring 102 no longer can bend back farther, as in FIG. 11, additional elements leading to $E^P$ can be added since width "w" of window 210 is deliberately made to be wider than the width "w'" of an element, shown in phantom in FIG. 12. As a result, when container 90a is full, FIG. 14, elements E and E', at least, occupy the upper volume of the container that would have had to be occupied by leaf spring 102a if it were a full wall element as in FIG. 11. (Cross-member 204 is adequate to hold the stacked elements in place.)

Figure 15:
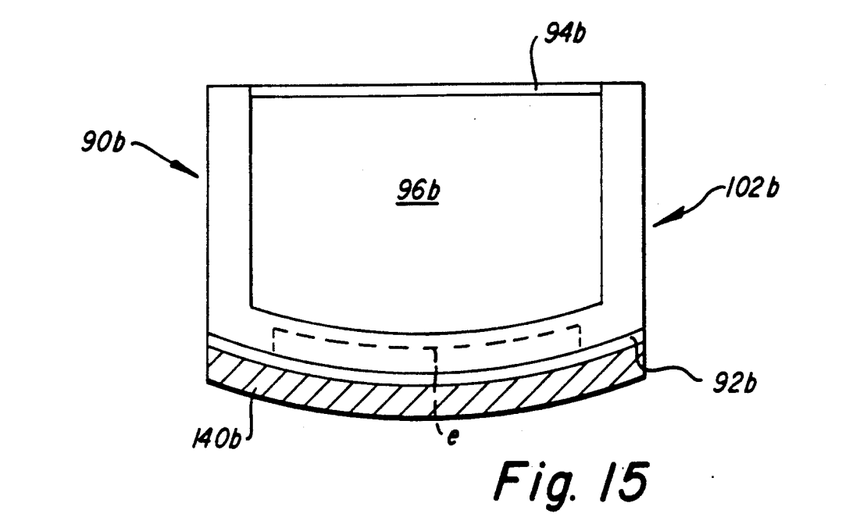
FIG. 15 and FIG. 16 are elevational views similar to that of FIG. 12, but of other embodiments.

From the preceding, it will be readily apparent that container 90 and 90a can be used to stack any members that are stackable, and not just used test elements from an analyzer. Furthermore, such elements need not be generally planar, although they certainly are in the preferred structure used with the analyzer. Curved elements or members can also be stacked in the container, as shown in FIG. 15. Parts similar to those previously described bear the same reference numerals to which the distinguishing suffix "b" is appended. Thus, container 90b has opposing end walls 92b and 94b, side wall 96b, and U-shaped leaf spring 102b as before. However, end wall 92b is concave, to accept dish-shaped element "e". Otherwise, container 90b is shaped and functions exactly as container 90a. If such container needs to be mounted at a stacking station as in an analyzer, frame 140b can be curved in a similar fashion, as shown.

Figure 16:
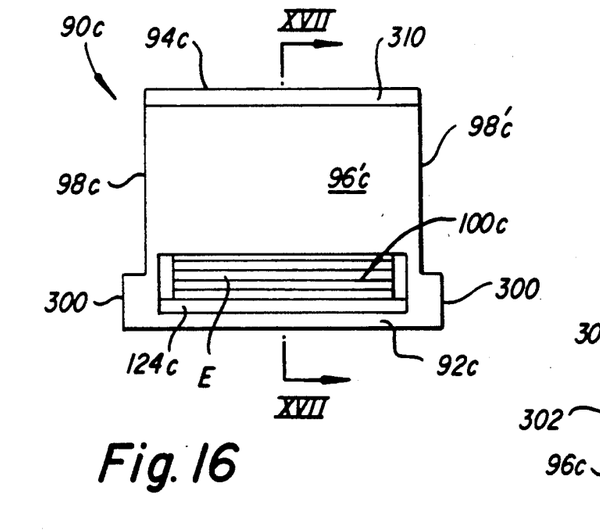
Figure 17:
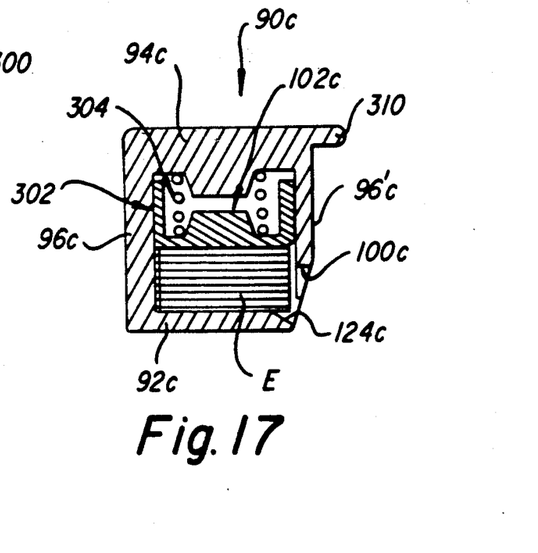
FIG. 17 is a section view taken generally along line XVII—XVII of FIG. 16.

Still other kinds of biasing means are useful in the container, besides a leaf spring, as shown in the embodiment of FIGS. 16 and 17. Parts similar to those previously described bear the same reference numerals, to which the distinguishing suffix "c" is applied.

Thus, container 90c comprises end walls 92c and 94c, FIG. 17, opposing side walls 98c and 98'c, FIG. 16, and another pair of side walls 96c and 96'c. Ramp surface 124c is part of end wall 92c, FIG. 17. Shoulders 300 are formed as extensions of side walls 98c and 98'c, FIG. 16, to allow the container to slip into the holding surfaces of the stacking station previously described. However, unlike the previous embodiment, biasing means 102c comprises a hollow member 302 biased downward by a compression spring 304 that presses against end wall 94c. Because of the limit in the amount of compression that is possible with spring 304, the percentage of the volume of container 90c that can be occupied by used test elements, is less than in previous embodiments. However, the advantage of such a device is more enclosure is provided of the used elements, which may be desirable if the liquids in the elements are particularly hazardous.

Lip 310 is used to aid in handling and orienting the container.

Alternatively, spring 304 of this embodiment can be conical in configuration, rather than cylindrical, to allow it to collapse on itself without occupying a lot of volume. Member 302 can also take on other shapes, including a flat disk.

Figure 18:
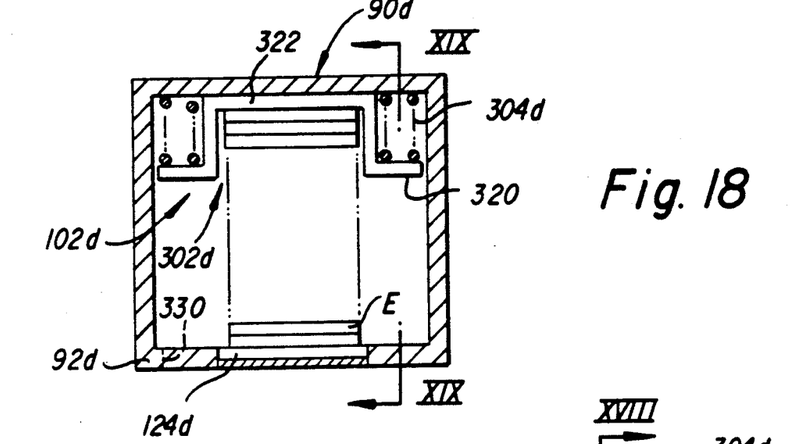
FIG. 18 is a section view of a container, similar to the section view of FIG. 7, but of another embodiment, taken generally along line XVIII—XVIII of FIG. 19.
Figures 19, 20:
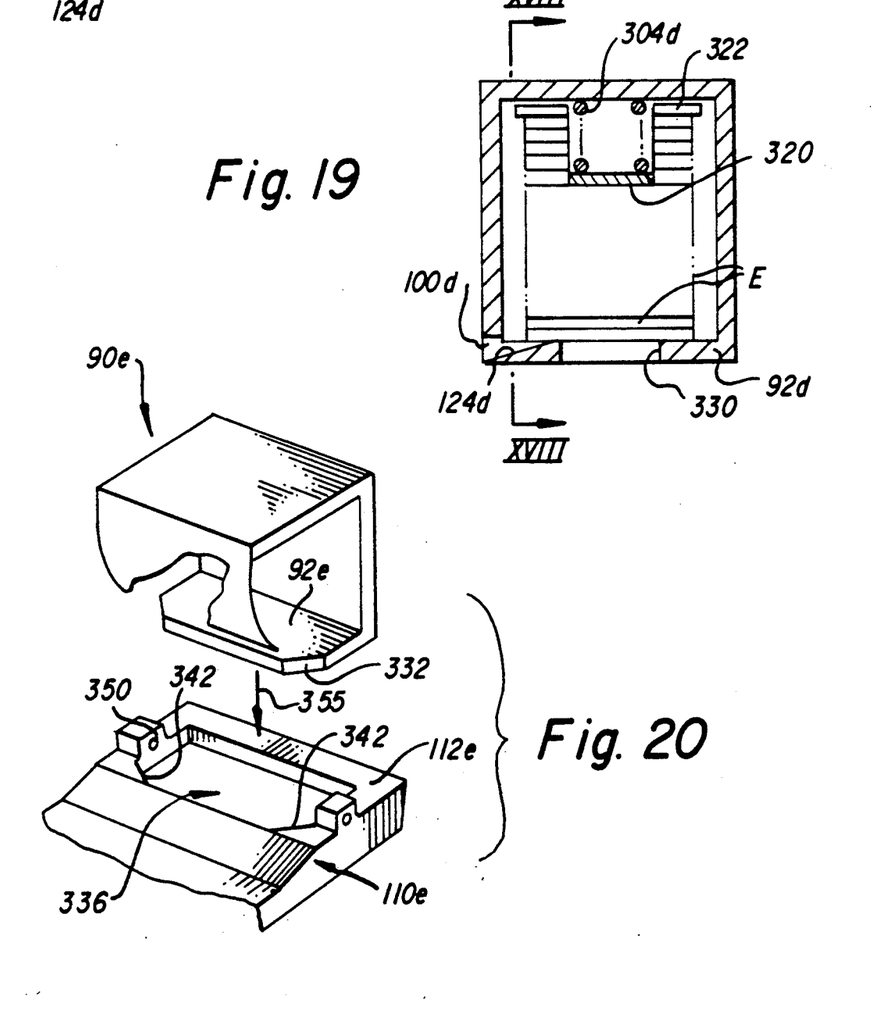
FIG. 19 is a section view taken generally along line XIX—XIX of FIG. 18.
FIG. 20 is a fragmentary perspective view of yet another embodiment of the container and stacking station.

To avoid the disadvantage noted above for container 90c, it can be constructed with a different shaped member 302, as shown in FIGS. 18 and 19. Parts similar to those previously described bear the same reference numeral with the letter "d" appended thereto. Thus, container 90d has an access aperture 100d with a built-in ramp surface 124d to receive test elements E under a spring-biased element 102d that uses one or more compression spring(s) 304d. However, unlike the previous embodiment, member 302d is hat-shaped to allow a full stack of test elements, as shown. Lower portions 320 of member 302d contact the springs. Slots 330 are formed in end wall 92d to allow the lower portions 320 of member 302d to protrude when member 302d is at or near the end of its travel, as when the first test element enters.

The container can also be lowered into place, FIG. 20, in the stacking station, rather than slid into place as suggested in FIG. 6. Parts similar to those previously described bear the same reference numeral, to which the distinguishing suffix "e" has been appended.

Thus, container 90e is constructed similarly to that of the embodiment of FIG. 6, except that end wall 92e has chamfered corners 332. Support 112e of stacking station 110e is the same as that of FIG. 6, except that it is provided with a mating depression 336 that will receive end wall 92e in a snap-fit. Thus, depression 336 includes chamfered corners 342. Spring-biased ball-detents 350 releasably hold the container in place by snapping over the edge of end wall 92e when container 90e is lowered into place, arrow 355.

It is not essential that the relative limited vertical movement between the stacking container, and the guide surface of the track, occur by camming the stacking station downward. Rather, the stacking station and its container can be fixed in place, and the upper plate above the guide surface can be movable upward, thus providing relative (downward) movement of the container, FIG. 21. Parts similar to those previously described bear the same reference numeral to which the distinguishing suffix "f" has been appended.

Figure 21:
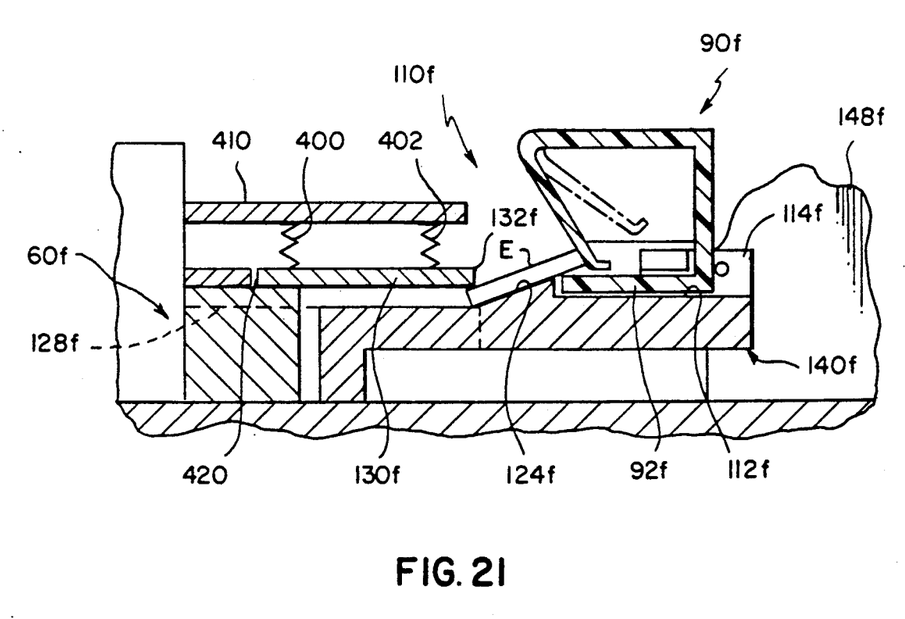
FIG. 21 is a section view similar to that of FIG. 6, but of still another embodiment.

Thus, FIG. 21, a container 90f is positioned in stacking station 110f, into which element-guiding surface 128f feeds from station 60f, as described for previous embodiments. (Container 90f can take any of the previously described forms.) Container 90f is held in place on surface 112f, adjacent wall 114f, to receive element E off ramp surface 124f, as described above. However, the limited relative downward movement (arrow 150 in FIG. 10) of the bottom wall 92f of container 90f, relative to incoming elements E, is achieved by letting cover 130f of guide surface 128f, be movable upward a slight distance, with stacking station 110f being fixed relative to guide surface 128f. Cover 130f in turn is preferentially biased downward to the position shown in FIG. 21 by compression springs 400, 402 that press against fixed lever arm 410.

Alternatively (not shown), cover 130f can be pivotally attached to the analyzer frame at its end 420, so that only the aperture end 132f is cammed upward by an advancing slide. In that case, spring 400 can be optionally omitted.

In the case of the upwardly movable cover 130f, care should be exercised to construct pusher blade 25 (shown only in FIG. 1) to be sufficiently rigid as to not ride over or under a test element that is to be pushed by the blade over guide surface 128f and under cover 130f.

Alternatively, the entire track assembly including guide surface 128f and cover 130f can be movable upward a slight distance, or the entire assembly can be pivoted at its end 420.

The invention has been described in detail with particular reference to preferred embodiments thereof, but it will be understood that variations and modifications can be effected within the spirit and scope of the invention.

What is claimed is:

1. Automatic collection apparatus for test elements useful in an analyzer to measure analytes in a biological liquid, said apparatus comprising a container having side walls, first and second end walls, access means in one of said side walls near said first end wall defining an aperture to allow test elements to feed into said container, and biasing means for biasing a test element against said first end wall or against a test element adjacent to said first end wall, and a stacking station for inserting test elements into said container, said station including means for releasably holding said container in position to receive used test elements, and guide means for guiding used test elements into said container in an ordered array, said guide means comprising a stationary track, means for providing relative limited vertical movement between said station and said track, between first and second limits; and means for biasing either said stacking station or said track against one of said limits, said stacking station including a camming surface shaped and positioned relative to said track to cause said stacking station a) to move against said biasing means when a test element first contacts said camming surface from said track, b) to receive said contacting test element, and c) to allow said stacking station to return under the action of said biasing means after loading said contacting test element, with said loaded test element positioned out of the plane of said track, whereby used test elements are loaded in said ordered array.

2. Apparatus as defined in claim 1, wherein said biasing means comprise a spring extending from one of said walls towards said bottom wall.

3. Apparatus as defined in claim 2, wherein said spring is a leaf spring extending from the one of said side walls in which is located said aperture.

4. Apparatus as defined in claim 1, wherein said biasing means is one of said side walls constructed as a leaf spring.

5. Apparatus as defined in claim 4, wherein said leaf spring is U-shaped, comprising two legs attached to the other of said end walls and a cross-member joining said legs, and having an aperture wider than the width of test elements held by said biasing means, so that test elements can be stacked in the container to occupy the volume said one side wall comprising said leaf spring, would have occupied if it were solid.

6. In an analyzer for testing analytes in a liquid patient sample in a test element containing reagents, the analyzer including means for incubating a test element to which a patient sample has been added, means for reading a detectable signal generated by a test element in response to the added patient sample, and means for moving a test element through the analyzer, including from said incubating means to said reading means, the improvement wherein the analyzer further includes automatic collection apparatus disposed downstream from said reading means to receive used test elements from said reading means, said apparatus comprising a container having side walls, first and second end walls, access means in one of said side walls near said first end wall defining an aperture to allow test elements to feed into said container, and biasing means for biasing a test element against said first end wall or against a test element adjacent to said first end wall, and a stacking station for inserting test elements into said container, said station including means for releasably holding said container in position to receive used test elements, and guide means for guiding used test elements into said container in an ordered array.

7. An analyzer as defined in claim 6, wherein said guide means comprise a stationary track, means for mounting said stacking station for limited vertical movement with respect to said track, between first and second limits; and means for biasing said stacking station against one of said limits, said stacking station including a camming surface shaped and positioned relative to said track to cause said stacking station a) to move against said biasing means when a test element first contacts said camming surface from said track, b) to receive said contacting test element, and c) to allow said stacking station to return under the action of said biasing means after loading said contacting test element, with said loaded test element positioned out of the plane of said track, whereby used test elements are loaded in said ordered array.

8. An analyzer as defined in claim 6 or 7, wherein said guide means causes said ordered array to comprise the first-in test element in contact with said biasing means and the last-in test element in contact with said first end wall.

9. An analyzer as defined in claim 6 or 7, wherein said biasing means comprise a spring extending from one of said walls towards said bottom wall.

10. An analyzer as defined in claim 6, and further including restricting means in said guide means for keeping test elements within said guide means even in the absence of gravity, whereby the analyzer is useful in a space station.

11. A method of collecting used test elements in an ordered array as they exit from a read station in an analyzer to a collection container having a hold-down spring, the method comprising the steps of a) supplying a collection container having side walls, first and second end walls, access means in one of said side walls near said first end wall defining an aperture to allow test elements to feed into said container, and a biasing means including a hold-down spring for biasing a test element adjacent to said first end wall;

b) inserting a first used test element into said container adjacent one end and under said spring so that a portion of said first element projects from said container;

c) inserting a next used test element into said container under said first test element by inserting it under said projecting portion and pushing said first test element against said spring; and d) inserting successive used test elements into said container so that they each enter under the last one in, until the container is full.

12. A method as described in claim 11, wherein said container is pivoted for slight vertical movement, and as an element enters said container, such entering element forces the container to pivot downwardly to aid in inserting the entering element against said hold-down spring.

13. In a container for holding test elements used in an analyzer to determine analytes in a liquid, the container including side walls, two opposing end walls, means defining an infeed access aperture in one of said side walls near one of said end walls, sized to allow a test element to enter the container, and biasing means for biasing a test element within said container, against said one end wall or another test element adjacent to said one end wall;

the improvement wherein said biasing means is one of said side walls constructed as a leaf spring.

14. A container as defined in claim 13, wherein said leaf spring is U-shaped, comprising two legs attached to the other of said end walls and a cross-member joining legs, and having an aperture wider than the width of test elements held by said biasing means, so that test elements can be stacked in the container to occupy the volume that said one side wall comprising said leaf spring would have occupied if it were solid.

15. A container for holding stackable members; comprising two opposing end walls, one of which is constructed to contact a member stacked in said container, a side wall joining said end walls, and opposite to said side wall, as the sole side wall on that side of the container, a leaf spring extending from one of said end walls towards, but not joined with, the opposite end wall.

16. A container as defined in claim 15, wherein said side wall is the only wall integrally joining said opposing end walls.

17. A container as defined in claims 15 or 16, wherein said leaf spring is U-shaped, comprising two legs joined to said one end wall and a cross-member joining said legs.

18. A container as defined in claims 13 or 15, wherein said one end wall includes a ramp surface for guiding a test element or a member into the container.

* * * * *

UNITED STATES PATENT AND TRADEMARK OFFICE
CERTIFICATE OF CORRECTION

PATENT NO. : 5,053,198

DATED : October 1, 1991

INVENTOR(S) : Quenin

It is certified that error appears in the above-identified patent and that said Letters Patent is hereby corrected as shown below:

Column 11, line 7, insert --said-- after "joining".

Signed and Sealed this

Sixth Day of April, 1993

*Attest:*

STEPHEN G. KUNIN

*Attesting Officer*     *Acting Commissioner of Patents and Trademarks*